United States Patent
Miyake et al.

(10) Patent No.: US 8,829,255 B1
(45) Date of Patent: Sep. 9, 2014

(54) (Z,Z,E)-1-CHLORO-6,10,12-PENTADECATRIENE AND METHOD FOR PREPARING (Z,Z,E)-7,11,13-HEXADECATRIENAL BY USING SAME

(71) Applicant: Shin-Etsu Chemical Co., Ltd., Tokyo (JP)

(72) Inventors: Yuki Miyake, Joetsu (JP); Miyoshi Yamashita, Joetsu (JP); Takehiko Fukumoto, Joetsu (JP); Naoki Ishibashi, Joetsu (JP)

(73) Assignee: Shin-Etsu Chemical Co., Ltd. (JP)

( * ) Notice: Subject to any disclaimer, the term of this patent is extended or adjusted under 35 U.S.C. 154(b) by 0 days.

(21) Appl. No.: 14/189,220

(22) Filed: Feb. 25, 2014

(30) Foreign Application Priority Data

Mar. 14, 2013 (JP) ................ 2013-051711

(51) Int. Cl.
*C07C 21/18* (2006.01)
*C07C 17/00* (2006.01)
*C07C 47/02* (2006.01)
*C07C 45/00* (2006.01)
*C07C 17/26* (2006.01)
*C07C 21/215* (2006.01)

(52) U.S. Cl.
CPC ............... *C07C 21/215* (2013.01); *C07C 17/26* (2013.01)
USPC ........... 570/189; 570/193; 568/448; 568/449; 568/485

(58) Field of Classification Search
USPC .................. 570/189, 193; 568/448, 449, 485
See application file for complete search history.

(56) References Cited

PUBLICATIONS

Leal et al. "Identification, Synthesis, and Field Evaluation of the Sex Pheromone from the Citrus Leafminer, *Phyllocnistis citrella*", *J. Chem. Ecology* 32(1):155-168 (2006).

Moreira et al. "Identification, Synthesis, and Field Testing of the Sex Pheromone from the Citrus Leafminer, *Phyllocnistis citrella*", *J. Chem. Ecology* 32(1):169-194 (2006).

Van Vang et al. "7,11,13-Hexadecatrienal identified from female moths of the citrus leafminer as a new sex pheromone component: synthesis and field evaluation in Vietnam and Japan", *J. Pestic. Sci.* 33(2):152-158 (2008).

*Primary Examiner* — Jafar Parsa

(74) *Attorney, Agent, or Firm* — Myers Bigel Sibley & Sajovec, P.A.

(57) ABSTRACT

Provided are (Z,Z,E)-1-chloro-6,10,12-pentadecatriene that can be synthesized without an oxidation reaction and a method for preparing (Z,Z,E)-7,11,13-hexadecatrienal by using (Z,Z,E)-1-chloro-6,10,12-pentadecatriene while not using an oxidation reaction. More specifically, provided is a method for preparing (Z,Z,E)-7,11,13-hexadecatrienal including a step of reacting a Grignard reagent into which (Z,Z,E)-1-chloro-6,10,12-pentadecatriene is converted with ethyl orthoformate to obtain (Z,Z,E)-1,1-diethoxy-7,11,13-hexadecatriene, and a step of treating the (Z,Z,E)-1,1-diethoxy-7,11,13-hexadecatriene with an acid to obtain (Z,Z,E)-7,11,13-hexadecatrienal.

3 Claims, No Drawings

(Z,Z,E)-1-CHLORO-6,10,12-PENTADECATRIENE AND METHOD FOR PREPARING (Z,Z,E)-7,11,13-HEXADECATRIENAL BY USING SAME

RELATED APPLICATION

This application claims priority from Japanese Patent Application No. 2013-051711, filed Mar. 14, 2013, the disclosure of which is incorporated by reference herein in its entirety.

FIELD AND BACKGROUND OF THE INVENTION

The present invention relates to a method for preparing (Z,Z,E)-7,11,13-hexadecatrienal, which is a sex pheromone substance of the citrus leafminer, a pest of citrus, by using (Z,Z,E)-1-chloro-6,10,12-pentadecatriene.

The citrus leafminer (*Phyllocnistis citrella*) is an important pest of citrus. It is parasitic and causes damage in young leaves and thereby has a serious influence on the growth of nursery trees. Its feeding damage marks accelerate occurrence of citrus canker. This pest mines the undersurface of leaves so that it cannot be controlled easily by pesticides. Its resistance to pesticides is also observed. Biological control methods have therefore been attracting attentions and a method of using a sex pheromone substance is expected as one of them.

It has been identified (W. S. Leal et al., J. Chem. Ecol. 32(1), 155-168 (2006)) that the sex pheromone composition of the citrus leafminer contains (Z,Z,E)-7,11,13-hexadecatrienal, (Z,Z)-7,11-hexadecadienal, and (Z)-7-hexadecenal as the main component, the second component, and the third component, respectively. Further, a 3:1 mixture of (Z,Z,E)-7,11,13-hexadecatrienal and (Z,Z)-7,11-hexadecadienal has been shown to have higher attractiveness than the main component alone (W. S. Leal et al., J. Chem. Ecol. 32(1), 155-168 (2006) and T. Ando et al., J. Pestic. Sci., 33(2), 152-158 (2008)).

Several preparation methods for synthesizing the sex pheromone substance (Z,Z,E)-7,11,13-hexadecatrienal have been reported. For example, it has been reported (W. S. Leal et al., J. Chem. Ecol. 32(1), 155-168 (2006)) that the sex pheromone substance can be obtained through a Wittig reaction between 10-(1,3-dioxan-2-yl)-(Z)-4-decenal and (Z)-2-pentenyltriphenylphosphonium bromide, followed by deprotection of acetal. It has also been reported (T. Ando et al., J. Pestic. Sci., 33(2), 152-158 (2008) and J. G. Millar et al., J. Chem. Ecol., 32(1), 169-194 (2006)) that the sex pheromone substance can be obtained through oxidation of (Z,Z,E)-7,11,13-hexadecatrienol with pyridinium chlorochromate and then separation of an isomer at 11-position by the subsequent purification with a silver nitrate column.

SUMMARY OF THE INVENTION

Any of the preparation methods thus reported, however, uses an oxidation reaction as a key reaction. The oxidation reaction often involves a risk of explosion or the like, and in an industrial scale, it has difficulty in isolating an aldehyde, which is a reaction product, with high purity and high yield.

With the foregoing in view, the present invention has been made. An object of the invention is to provide (Z,Z,E)-1-chloro-6,10,12-pentadecatriene that can be synthesized without an oxidation reaction and a method for preparing (Z,Z,E)-7,11,13-hexadecatrienal by using the (Z,Z,E)-1-chloro-6,10,12-pentadecatriene, the method therefore not comprising a step of an oxidation reaction.

In the invention, it has been found that (Z,Z,E)-1-chloro-6,10,12-pentadecatriene can be mass-produced at a low cost, and (Z,Z,E)-7,11,13-hexadecatrienal can be obtained with high purity and at high yield by converting the (Z,Z,E)-1-chloro-6,10,12-pentadecatriene into a corresponding Grignard reagent, conducting a coupling reaction between the Grignard reagent and ethyl orthoformate, and then conducting a hydrolysis treatment, leading to the completion of the invention.

In one aspect of the invention, there is provided (Z,Z,E)-1-chloro-6,10,12-pentadecatriene. In another aspect of the invention, there is also provided a method for preparing (Z,Z,E)-1-chloro-6,10,12-pentadecatriene comprising a step of chlorinating (Z,Z,E)-3,7,9-dodecatrien-1-ol into (Z,Z,E)-1-chloro-3,7,9-dodecatriene and a step of reacting a Grignard reagent into which the (Z,Z,E)-1-chloro-3,7,9-dodecatriene is converted with 1-bromo-3-chloropropane. In a further aspect of the invention, there is also provided a method for preparing (Z,Z,E)-7,11,13-hexadecatrienal comprising a step of reacting a Grignard reagent into which (Z,Z,E)-1-chloro-6,10,12-pentadecatriene is converted with ethyl orthoformate to obtain (Z,Z,E)-1,1-diethoxy-7,11,13-hexadecatriene, and a step of treating the (Z,Z,E)-1,1-diethoxy-7,11,13-hexadecatriene with an acid to obtain (Z,Z,E)-7,11,13-hexadecatrienal.

According to the invention, none of the steps require an oxidation reaction so that (Z,Z,E)-7,11,13-hexadecatrienal can be mass-produced at a low cost with high reliability.

Moreover, according to the invention, (Z,Z,E)-7,11,13-hexadecatrienal can be prepared efficiently by coupling the Grignard reagent obtained from (Z,Z,E)-1-chloro-6,10,12-pentadecatriene with ethyl orthoformate.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

(Z,Z,E)-1-Chloro-6,10,12-pentadecatriene (3) can be prepared, for example, by chlorination of (Z,Z,E)-3,7,9-dodecatrien-1-ol (1), a subsequent conversion of the resulting product into a corresponding Grignard reagent, and a reaction of the Grignard reagent with 1-bromo-3-chloropropane.

The (Z,Z,E)-3,7,9-dodecatrien-1-ol (1), a starting material, can be prepared, for example, by a Wittig reaction between an ylide derived from 5-chloro-1-pentyne and 2-pentenal, an addition of carbon or carbons to the terminal alkyne, and hydrogenation of the triple bond. The hydrogenation of the carbon-carbon triple bond into a carbon-carbon double bond can be achieved using a known catalyst, for example, a P2-nickel catalyst.

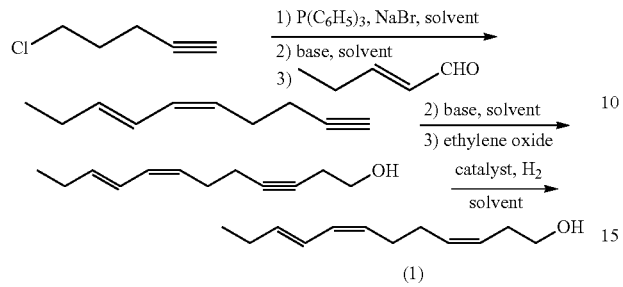

(1)

The (Z,Z,E)-3,7,9-dodecatrien-1-ol (1) thus obtained can be reacted with a chlorinating agent to produce (Z,Z,E)-1-chloro-3,7,9-dodecatriene (2). This chlorination reaction can be conducted, for example, by reacting the (Z,Z,E)-3,7,9-dodecatrien-1-ol (1) with a chlorinating agent in a solvent in the presence of a base.

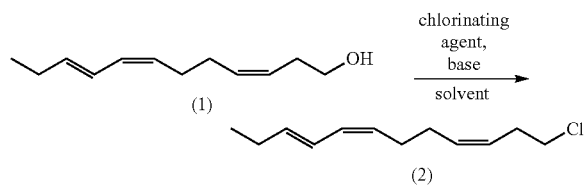

Examples of the chlorinating agent include thionyl chloride, sulfuryl chloride, methanesulfonyl chloride, p-toluenesulfonyl chloride, benzenesulfonyl chloride, phosphorus trichloride, and phosphorus pentachloride. Methanesulfonyl chloride is preferred from the standpoint of isomerization. The chlorinating agent can be used in an amount of preferably from 1.0 to 1.6 mol per mol of the (Z,Z,E)-3,7,9-dodecatrien-1-ol (1). When the amount is less than 1.0 mol, the reaction may not proceed smoothly. When the amount is more than 1.6 mol, some of the chlorinating agent may be wasted.

Examples of the base to be used for the chlorination reaction include pyridine-based compounds or pyridines such as pyridine and collidine; alkylamine compounds such as triethylamine, tributylamine and N,N-diisopropylethylamine; and aniline compounds such as aniline and N,N-diethylaniline. Pyridine is preferred from the standpoint of reactivity. The base can be used in an amount of preferably from 1.0 to 2.2 mol per mol of the (Z,Z,E)-3,7,9-dodecatrien-1-ol (1). When the amount is less than 1.0 mol, the reaction may not proceed smoothly. When the amount is more than 2.2 mol, some of the base may be wasted.

Examples of the solvent to be used for the chlorination reaction include hydrocarbon-based solvents such as toluene and hexane; ether-based solvents such as tetrahydrofuran and diethyl ether; and polar solvents such as N,N-dimethylformamide, N,N-dimethylacetamide and dichloromethane. N,N-dimethylformamide is preferred from the standpoint of reactivity. The solvent is used in an amount of preferably from 50 to 500 g per mol of the (Z,Z,E)-3,7,9-dodecatrien-1-ol (1). When the amount is less than 50 g, the reaction may not proceed smoothly. When the amount is more than 500 g, some of the solvent may be wasted, and an amount of the reactants may have to be reduced.

The reaction temperature to be used for the chlorination reaction is preferably from 5 to 70° C. When the temperature is less than 5° C., the reaction may not be completed. When the temperature is more than 70° C., the amount of an impurity may increase.

The (Z,Z,E)-1-chloro-3,7,9-dodecatriene (2) is converted into a corresponding Grignard reagent and then the Grignard reagent is reacted with 1-bromo-3-chloropropane to obtain (Z,Z,E)-1-chloro-6,10,12-pentadecatriene (3).

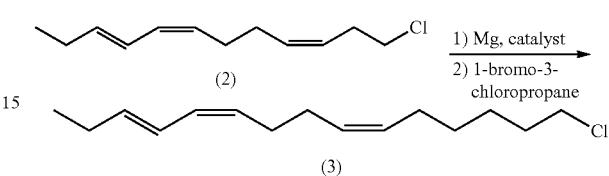

The Grignard reagent can be prepared by reacting the (Z,Z,E)-1-chloro-3,7,9-dodecatriene (2) with magnesium in a solvent.

Examples of the solvent include hydrocarbon-based solvents such as toluene and hexane, and ether-based solvents such as tetrahydrofuran and diethyl ether. Tetrahydrofuran is preferred from the standpoint of a reaction rate for producing the Grignard reagent. The solvent can be used in an amount of preferably from 200 to 450 g per mol of the (Z,Z,E)-1-chloro-3,7,9-dodecatriene (2).

Magnesium can be used in an amount of preferably from 1.0 to 1.5 mol per mol of the (Z,Z,E)-1-chloro-3,7,9-dodecatriene (2).

Examples of the catalyst to be used for the coupling reaction with the Grignard reagent include copper halides such as cuprous chloride, cupric chloride, cuprous bromide, cupric bromide, cuprous iodide and cupric iodide. Cuprous iodide is preferred from the standpoint of reactivity. The catalyst can be used in an amount of preferably from 0.003 to 0.03 mol per mol of the (Z,Z,E)-1-chloro-3,7,9-dodecatriene (2).

The catalyst to be used for the coupling reaction with the Grignard reagent is preferably used together with a cocatalyst. Examples of the cocatalyst include phosphorus compounds such as triethyl phosphite and triphenylphosphine. Triethyl phosphite is preferred from the standpoint of reactivity. The cocatalyst can be used in an amount of preferably from 0.001 to 0.05 mol per mol of the (Z,Z,E)-1-chloro-3,7,9-dodecatriene (2).

Examples of the solvent to be used for the coupling reaction with the Grignard reagent include hydrocarbon-based solvents such as toluene and hexane, and ether-based solvents such as tetrahydrofuran and diethyl ether. Tetrahydrofuran is preferred from the standpoint of reactivity. The solvent can be used in an amount of preferably from 50 to 300 g per mol of the (Z,Z,E)-1-chloro-3,7,9-dodecatriene (2).

The reaction temperature to be used for the coupling reaction with the Grignard reagent is preferably from 0 to 30° C. When the reaction temperature is less than 0° C., the reaction may not proceed smoothly. When the reaction temperature is more than 30° C., a side reaction may take place.

Next, a method for preparing (Z,Z,E)-7,11,13-hexadecatrienal (5) by using the (Z,Z,E)-1-chloro-6,10,12-pentadecatriene(3) thus obtained will be described.

First, the (Z,Z,E)-1-chloro-6,10,12-pentadecatriene(3) is converted into a corresponding Grignard reagent, and then subjected to the reaction with ethyl orthoformate to produce (Z,Z,E)-1,1-diethoxy-7,11,13-hexadecatriene (4).

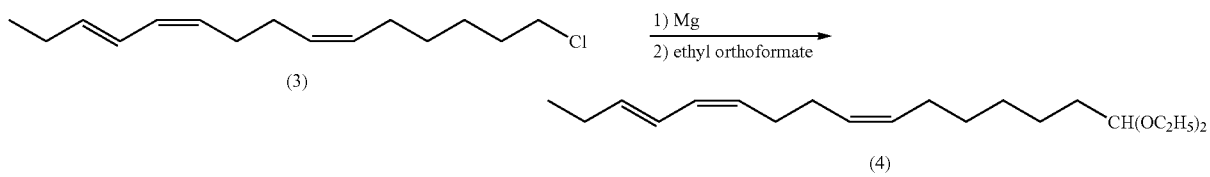

(3)

(4)

The Grignard reagent can be prepared by reacting the (Z,Z,E)-1-chloro-6,10,12-pentadecatriene (3) with magnesium in a solvent.

Examples of the solvent include hydrocarbon-based solvents such as toluene and hexane, and ether-based solvents such as tetrahydrofuran and diethyl ether. Tetrahydrofuran is preferred from the standpoint of a reaction rate for producing the Grignard reagent. The solvent can be used in an amount of preferably from 200 to 450 g per mol of the (Z,Z,E)-1-chloro-6,10,12-pentadecatriene (3).

Magnesium can be used in an amount of preferably from 1 to 1.5 mol per mol of the (Z,Z,E)-1-chloro-6,10,12-pentadecatriene (3).

Examples of the solvent to be used for the coupling reaction with the Grignard reagent include hydrocarbon-based solvents such as toluene and hexane, and ether-based solvents such as tetrahydrofuran and diethyl ether. A mixed solvent of tetrahydrofuran and toluene is preferred from the standpoint of reactivity. The solvent can be used in an amount of preferably from 100 to 800 g per mol of the (Z,Z,E)-1-chloro-6,10,12-pentadecatriene (3).

The reaction temperature to be used for the coupling reaction with the Grignard reagent is preferably from 75 to 115° C. When the reaction temperature is less than 75° C., the reaction may not proceed smoothly. When the reaction temperature is more than 115° C., the solvent may evaporate.

Finally, the (Z,Z,E)-1,1-diethoxy-7,11,13-hexadecatriene (4) is treated with an acid to produce (Z,Z,E)-7,11,13-hexadecatrienal (5). This reaction proceeds smoothly by distilling off ethanol, which is a by-product, through a distillation column attached to a reaction vessel, and no isomerization between E and Z isomers can be found during the reaction. For example, the (Z,Z,E)-1,1-diethoxy-7,11,13-hexadecatriene (4) is treated with an acid in a solvent to hydrolyze the acetal group.

When, for example, 10% by weight hydrochloric acid is used as the acid, its amount is preferably from 100 to 150 g per mol of the (Z,Z,E)-1,1-diethoxy-7,11,13-hexadecatriene (4).

Examples of the solvent to be used for the acid treatment include hydrocarbon-based solvents such as toluene and hexane; various alcohol solvents such as methanol and ethanol; ether-based solvents such as tetrahydrofuran and diethyl ether; and polar solvents such as dichloromethane. Toluene is preferred from the standpoint of reactivity. The solvent is used in an amount of preferably 300 g or less per mol of the (Z,Z,E)-1,1-diethoxy-7,11,13-hexadecatriene (4). When the amount is more than 300 g, some of the solvent may be wasted and an amount of the reactants may have to be reduced.

The reaction temperature to be used for the acid treatment is preferably from 5 to 30° C. When the reaction temperature is less than 5° C., the reaction may not proceed smoothly. When the reaction temperature is more than 30° C., the amount of an impurity may increase.

EXAMPLES

The invention will hereinafter be described specifically by Examples, but it is not limited to or by the Examples.

Example 1

Preparation of (Z,Z,E)-1-chloro-3,7,9-dodecatriene (2)

(Z,Z,E)-3,7,9-Dodecatrien-1-ol (169.47 g, 0.94 mol), pyridine (134.2 g, 1.70 mol) and N,N-dimethylformamide (284 g) were placed in a reaction vessel, and stirred at 5 to 10° C. for 30 minutes. After stirring, methanesulfonyl chloride (151.2 g, 1.32 mol) was added dropwise thereto at 5 to 15° C. After completion of the dropwise addition, the reaction mixture

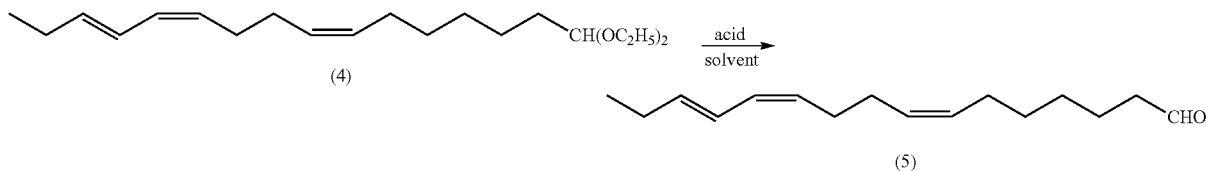

(4)

(5)

Examples of the acid include inorganic acids such as hydrochloric acid and hydrobromic acid, p-toluenesulfonic acid, trifluoroacetic acid, acetic acid, iodotrimethylsilane, and titanium tetrachloride. Hydrochloric acid is preferred from the standpoint of reactivity.

The acid to be used in the above reaction has a concentration of preferably from 5 to 50% by weight, more preferably from 10 to 37% by weight. When the concentration is less than 5% by weight, the reaction may not proceed smoothly. When the concentration is more than 50% by weight, severe control of temperature, pressure and the like may be required at the time when the acid is used.

was stirred at 60 to 65° C. for 2 hours. Then, water (471 g) was added to the reaction mixture to terminate the reaction. Hexane (471 g) was added thereto to separate the reaction mixture into phases. The organic phase was washed with hydrochloric acid and then with an aqueous sodium bicarbonate solution, and then concentrated by removal of the solvent under reduced pressure. The residue was distilled under reduced pressure to obtain (Z,Z,E)-1-chloro-3,7,9-dodecatriene (bp: 114 to 120° C./5 mmHg, 166.93 g, 0.84 mol) with a yield of 89.2%.

[Nuclear magnetic resonance spectrum] $^1$H-NMR (300 MHz, CDCl$_3$): δ 1.02 (3H, t), 2.08-2.19 (4H, m), 2.25 (2H, dt), 2.52 (2H, dt), 3.51 (2H, t), 5.30 (1H, dt), 5.41 (1H, dt), 5.55 (1H, dt), 5.72 (1H, dt), 5.98 (1H, dd), 6.28 (1H, dd); $^{13}$C-NMR (75.6 MHz, CDCl$_3$): δ13.57, 25.86, 27.49, 27.52, 30.70, 44.16, 124.47, 125.38, 128.69, 129.24, 132.26, 136.65

[Mass spectrum] EI-mass spectrum (70 eV): m/z 198(M$^+$), 95, 79, 67, 55, 41, 27

[Infrared absorption spectrum] (NaCl): νmax 2962, 2932, 2872, 1652, 1454, 1319, 983, 947, 740

Preparation of (Z,Z,E)-1-chloro-6,10,12-pentadecatriene (3)

Magnesium (13.7 g, 0.59 mol) and tetrahydrofuran (168 g) were placed in a reaction vessel, and stirred at 60 to 65° C. for 30 minutes. After stirring, (Z,Z,E)-1-chloro-3,7,9-dodecatriene (111.29 g, 0.56 mol) were added dropwise thereto at 60 to 65° C. and the reaction mixture was stirred at 70 to 75° C. for 2 hours to prepare (Z3,Z7,E9)-3,7,9-dodecatrienylmagnesium chloride.

Copper (I) iodide (1.03 g, 0.0054 mol), triethyl phosphite (2.34 ml, 0.014 mol), 1-bromo-3-chloropropane (92.29 g, 0.59 mol) and tetrahydrofuran (56 g) were added to the reaction vessel and the resulting mixture was stirred at 0 to 5° C. for 30 minutes. After stirring, the tetrahydrofuran solution of (Z,Z,E)-3,7,9-dodecatrienylmagnesium chloride prepared above was added dropwise to the reaction mixture at 5 to 15° C.

After completion of the dropwise addition, the resulting mixture was stirred at 5 to 10° C. for 40 minutes. Then, ammonium chloride (6.40 g), an aqueous 20% by weight hydrogen chloride solution (10.1 g) and water (175 g) were added to the reaction mixture to terminate the reaction thereof. The water phase was removed, while the organic phase was concentrated by removal of tetrahydrofuran under reduced pressure. The residue was then distilled under reduced pressure to obtain (Z,Z,E)-1-chloro-6,10,12-pentadecatriene (bp: 150 to 153° C./3 mmHg, 110.77 g, 0.46 mol) with a yield of 82.8%.

[Nuclear magnetic resonance spectrum] $^1$H-NMR (300 MHz, CDCl$_3$): δ1.02 (3H, t), 1.34-1.49 (4H, m), 1.78 (2H, tt), 2.02-2.16 (6H, m), 2.22 (2H, dt), 3.53 (2H, t), 5.27-5.34 (1H, m), 5.35-5.42 (2H, m), 5.72 (1H, dt), 5.97 (1H, dd), 6.28 (1H, dd); $^{13}$C-NMR (75.6 MHz, CDCl$_3$): δ13.60, 25.87, 26.50, 27.04, 27.22, 27.65, 27.77, 32.52, 45.04, 124.57, 128.99, 129.21, 129.34, 129.94, 136.44

[Mass spectrum] EI-mass spectrum (70 eV): m/z 240(M$^+$), 95, 79, 67, 55, 41, 29

[Infrared absorption spectrum] (NaCl): νmax 3006, 2933, 2857, 1652, 1460, 1311, 982, 946

Preparation of (Z,Z,E)-1,1-diethoxy-7,11,13-hexadecatriene (4)

Magnesium (5.65 g, 0.24 mol) and tetrahydrofuran (69 g) were placed in a reaction vessel, and stirred at 60 to 65° C. for 30 minutes. After stirring, (Z,Z,E)-1-chloro-6,10,12-pentadecatriene (55.39 g, 0.23 mol) was added dropwise thereto at 60 to 65° C. and the resulting mixture was stirred at 70 to 75° C. for 2 hours to prepare (Z,Z,E)-6,10,12-pentadecatrienylmagnesium chloride.

Toluene (119 g) and ethyl orthoformate (44.29 g, 0.30 mol) were added to the reaction vessel at 75 to 85° C. The resulting mixture was stirred at 90 to 100° C. for 8 hours. Then, an aqueous 20% by weight hydrogen chloride solution (21.8 g) and water (34.5 g) were added thereto to separate the reaction mixture into phases. The organic phase was washed with an aqueous sodium hydroxide solution, and concentrated by removal of the solvent under reduced pressure to obtain (Z,Z,E)-1,1-diethoxy-7,11,13-hexadecatriene (58.62 g, 0.19 mol) with a yield of 81.8%.

[Nuclear magnetic resonance spectrum] $^1$H-NMR (300 MHz, CDCl$_3$): δ1.01 (3H, t), 1.20 (6H, t), 1.28-1.38 (4H, m), 1.57-1.63 (2H, m), 1.99-2.05 (2H, m), 2.08-2.15 (4H, m), 2.21 (4H, dt), 3.48 (2H, q), 3.63 (2H, q), 4.47 (1H, t), 5.27-5.39 (3H, m), 5.70 (1H, dt), 5.96 (1H, t), 6.29 (1H, dd); $^{13}$C-NMR (75.6 MHz, CDCl$_3$): δ13.59, 15.33, 24.63, 25.86, 27.17, 27.32, 27.81, 29.12, 29.60, 33.53, 60.78, 102.90, 124.60, 128.93, 128.98, 129.23, 130.38, 136.37

[Mass spectrum] EI-mass spectrum (70 eV): m/z 262(M$^+$-46), 103, 95, 67, 47, 29

[Infrared absorption spectrum] (NaCl): νmax 2972, 2929, 2857, 1456, 1373, 1128, 1062, 982, 946, 735

Preparation of (Z,Z,E)-7,11,13-hexadecatrienal (5)

(Z,Z,E)-1,1-Diethoxy-7,11,13-hexadecatriene (49.36 g, 0.16 mol) and toluene (30 g) were placed in a reaction vessel and stirred at 20 to 25° C. for 30 minutes. After stirring, 10% by weight hydrochloric acid (19.3 g) was added dropwise to the reaction mixture at 20 to 25° C., and stirred for one hour. The reaction mixture was separated into phases. Then, the organic phase was washed with an aqueous sodium bicarbonate solution, and concentrated by removal of the solvent under reduced pressure to obtain (Z,Z,E)-7,11,13-hexadecatrienal (30.47 g, 0.13 mol) with a yield of 82.7%.

[Nuclear magnetic resonance spectrum] $^1$H-NMR (300 MHz, CDCl$_3$): δ1.01 (3H, t), 1.30-1.41 (4H, m), 1.63 (2H, tt), 2.00-2.07 (2H, m), 2.11 (4H, tt), 2.21 (2H, dt), 2.41 (2H, dt), 5.26-5.33 (3H, m), 5.70 (1H, dt), 5.96 (1H, dd), 6.29 (1H, dd), 9.75 (1H, t); $^{13}$C-NMR (75.6 MHz, CDCl$_3$): δ13.57, 21.94, 25.84, 26.97, 27.31, 27.74, 28.73, 29.36, 43.82, 124.55, 128.96, 129.13, 129.24, 129.99, 136.40, 202.9

[Mass spectrum] EI-mass spectrum (70 eV): m/z 234 (M$^+$), 95, 79, 67, 55, 41, 29

[Infrared absorption spectrum] (NaCl): νmax 2962, 2932, 2856, 1727, 1460, 1322, 983, 947, 739

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:

1. (Z,Z,E)-1-Chloro-6,10,12-pentadecatriene.

2. A method for preparing (Z,Z,E)-1-chloro-6,10,12-pentadecatriene, comprising:
   a step of chlorinating (Z,Z,E)-3,7,9-dodecatrien-1-o1 into (Z,Z,E)-1-chloro-3,7,9-dodecatriene, and
   a step of reacting a Grignard reagent into which the (Z,Z,E)-1-chloro-3,7,9-dodecatriene is converted with 1-bromo-3-chloropropane.

3. A method for preparing (Z,Z,E)-7,11,13-hexadecatrienal, comprising:
   a step of reacting a Grignard reagent into which (Z,Z,E)-1-chloro-6,10,12-pentadecatriene is converted with ethyl orthoformate to obtain (Z,Z,E)-1,1-diethoxy-7,11,13-hexadecatriene, and
   a step of treating the (Z,Z,E)-1,1-diethoxy-7,11,13-hexadecatriene with an acid to obtain (Z,Z,E)-7,11,13-hexadecatrienal.

* * * * *

UNITED STATES PATENT AND TRADEMARK OFFICE
CERTIFICATE OF CORRECTION

| | | |
|---|---|---|
| PATENT NO. | : 8,829,255 B1 | Page 1 of 1 |
| APPLICATION NO. | : 14/189220 | |
| DATED | : September 9, 2014 | |
| INVENTOR(S) | : Miyake et al. | |

It is certified that error appears in the above-identified patent and that said Letters Patent is hereby corrected as shown below:

In the Claims:
Column 8, Claim 2, Line 51: Correct "-1-01 into" to read -- -1-ol into --

Signed and Sealed this
Tenth Day of February, 2015

Michelle K. Lee
*Deputy Director of the United States Patent and Trademark Office*